(12) United States Patent
Youngs et al.

(10) Patent No.: US 12,106,468 B2
(45) Date of Patent: Oct. 1, 2024

(54) FOREIGN MATERIAL INSPECTION SYSTEM

(71) Applicant: Prospection Solutions, LLC, Kearney, MO (US)

(72) Inventors: Jeff Youngs, Kearney, MO (US); Kyle N. Knudsen, Kansas City, MO (US); Flippo Sani, Reggio Emilia (IT)

(73) Assignee: PROSPECTION SOLUTIONS, LLC, Kearney, MO (US)

( * ) Notice: Subject to any disclaimer, the term of this patent is extended or adjusted under 35 U.S.C. 154(b) by 0 days.

(21) Appl. No.: 17/061,217

(22) Filed: Oct. 1, 2020

(65) Prior Publication Data
US 2021/0100256 A1 Apr. 8, 2021

Related U.S. Application Data

(60) Provisional application No. 62/909,380, filed on Oct. 2, 2019.

(51) Int. Cl.
A22C 17/00 (2006.01)
G01N 21/88 (2006.01)
G01N 33/12 (2006.01)
G06T 5/30 (2006.01)
G06T 7/00 (2017.01)

(52) U.S. Cl.
CPC ............ G06T 7/001 (2013.01); A22C 17/008 (2013.01); G01N 21/8803 (2013.01); G01N 33/12 (2013.01); G06T 5/30 (2013.01); G06T 7/0004 (2013.01); G06T 2207/10024 (2013.01); G06T 2207/30128 (2013.01)

(58) Field of Classification Search
None
See application file for complete search history.

(56) References Cited

U.S. PATENT DOCUMENTS 5,115,475 A * 5/1992 Lebeau ................... G06T 7/001
257/E21.525
5,847,382 A 12/1998 Koch
(Continued)

FOREIGN PATENT DOCUMENTS

DK 180440 B1 * 9/2019 ............. A22C 17/00
JP 2005227029 8/2005
(Continued)

OTHER PUBLICATIONS

Schlezinger, U.S. Appl. No. 62/979,511, filed Feb. 21, 2020 with the USPTO, Specification included as NPL (Year: 2020).*
(Continued)

Primary Examiner — Emily C Terrell
Assistant Examiner — Nathan J Bloom
(74) Attorney, Agent, or Firm — SHUTTLEWORTH & INGERSOLL, PLC; Jason R. Sytsma

(57) ABSTRACT

A first conveyor for conveying foodstuff, a second conveyor separated from the first conveyor by a gap of free space, a top camera positioned above the gap and above the first conveyor and the second conveyor, a bottom camera positioned below the gap and below the first conveyor and the second conveyor, wherein the top camera and the bottom camera capture images of the foodstuff in the gap between the first conveyor and the second conveyor for analysis.

15 Claims, 8 Drawing Sheets

(56) References Cited

U.S. PATENT DOCUMENTS

| | | | | |
|---|---|---|---|---|
| 5,887,073 | A * | 3/1999 | Fazzari | G06K 9/6253 |
| | | | | 382/110 |
| 6,064,759 | A * | 5/2000 | Buckley | G01B 11/024 |
| | | | | 348/125 |
| 2010/0236994 | A1 * | 9/2010 | Hoffman | B07C 5/362 |
| | | | | 209/552 |
| 2015/0283586 | A1 * | 10/2015 | Dante | G06K 9/0063 |
| | | | | 209/577 |
| 2018/0198937 | A1 * | 7/2018 | Yoshizawa | H04N 1/00702 |
| 2019/0108396 | A1 * | 4/2019 | Dal Mutto | G06V 20/52 |
| 2020/0368788 | A1 * | 11/2020 | Jeindl | B07C 5/368 |
| 2021/0121922 | A1 * | 4/2021 | Schmidt | G06K 9/2036 |
| 2021/0262945 | A1 * | 8/2021 | Schlezinger | G01N 21/9508 |
| 2022/0237770 | A1 * | 7/2022 | Iwanaga | G06T 7/0004 |

FOREIGN PATENT DOCUMENTS

| | | | | |
|---|---|---|---|---|
| JP | | 2008541007 | 11/2008 | |
| JP | | 2012163485 | 8/2012 | |
| JP | | 2016217946 | 12/2016 | |
| JP | | 2017067622 | 4/2017 | |
| WO | WO-2006129391 | A1 * | 12/2006 | B07C 5/3422 |

OTHER PUBLICATIONS

JP2005227029—English Translation.
JP2012163485—English Translation.
JP2017067622—English Translation.
JP2016217946—English Translation.
JP2008541007—English Translation.
Aranca Search Report—Novelty Search—Meat Grinder—Jan. 21, 2020.

\* cited by examiner

FOREIGN MATERIAL INSPECTION SYSTEM

CROSS-REFERENCE TO RELATED APPLICATIONS

This application claims priority to U.S. Provisional Patent Application No. 62/909,380 filed on Oct. 2, 2019, the contents of which are hereby incorporated by reference herein.

TECHNICAL FIELD

This disclosure relates to foreign material inspection systems, and more specifically, this disclosure relates to multi-view inspection system for foodstuffs.

BACKGROUND INFORMATION

Physical contamination is one of the major types of contamination compromising food safety. In meat and other foodstuffs, physical hazards include plastic, metal, glass, bone fragments, etc., which can lead to serious injury if ingested by the consumer. To ensure food quality and food safety, it is necessary for meat processors to inspect each piece of meat and to make sure that bone fragments and any other unwanted hazardous materials such as metals and plastics do not remain in the product.

Imaging technologies have been adopted by researches for detecting foreign material in food products. X-ray imaging techniques, as noninvasive inspection methods, have been used for years to detect physical contamination in food products. However, traditional x-ray inspection systems currently being used to detect bone fragments in meat have a high rate of failure (over 30%). Laser irradiation imaging has been used in which a laser beam is used to scan food products. However, such systems also have a higher failure rate than desired, since they are not capable of capturing a true profile of the surface of a meat product due to undetected surface bumps or other hidden occlusions on the surface.

Vision systems have been developed based on optical measurement using a light source or multiple light sources to illuminate a material to be inspected and a digital image sensor to sense visible characteristics of the material to be inspected, such as material integrity or grade of the material. In such systems, digital image sensor elements are typically exposed to light transmitted through the continuous web of material or reflected from the surface of the material. These systems are highly accurate but can only inspect one side of the meat at a time.

Accordingly, there is a need for a foreign material inspection system that uses machine vision technology and can inspect both sides of the meat substantially simultaneously.

SUMMARY

Disclosed is a foodstuff inspection system and method of inspecting food. The system comprises of a first conveyor for conveying foodstuff, a second conveyor separated from the first conveyor by a gap of free space, a top camera positioned above the gap and above the first conveyor and the second conveyor, a bottom camera positioned below the gap and below the first conveyor and the second conveyor, wherein the top camera and the bottom camera capture images of the foodstuff in the gap between the first conveyor and the second conveyor for analysis.

In some embodiments, the system comprises a processor connected to the top camera and the bottom camera for processing images taken of the foodstuff for detection of foreign debris in the foodstuff. A library communicatively coupled to the processor containing data representative of acceptable pixels corresponding to images of foodstuff is provided, wherein the processor compares images of the foodstuffs on a pixel by pixel basis with the data representative of acceptable pixels stored in the library to detect foreign debris. The processor conducts a morphological operation on the image of the foodstuff to emphasize foreign debris before the processor compares the image of the foodstuff, which can comprise image dilation to make foreign debris more visible. The processor also scans the image of the foodstuff both vertically and horizontally to detect groups of adjacent pixels corresponding to foreign debris, wherein the group of adjacent pixels below a threshold number of pixels is ignored to prevent false negatives.

In one implementation, the top camera and the bottom camera take simultaneous images of the respective top side and the bottom side of the foodstuff. The top camera and the bottom camera capture colored rbg images for analysis.

In another implementation the system is provided with a rejection system communicatively coupled to the processor wherein when a group of pixels in the image of the foodstuff is determined to be consistent with foreign debris, the foodstuff is tracked by the rejection system for removal. The rejection system uses the speed of the second conveyor, the length of the second conveyor, and the time of acquisition of the image of the foodstuff to track the foodstuff for removal.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

In accordance with one aspect of the present invention, disclosed is a 360° Low Density Foreign Material Inspection System designed to detect and reject visible Low-Density Foreign Material from Foodstuff. The system operates by inspecting the top and bottom and sides of products at the same time. The inspection takes place in a gap in-between two conveyors. The inspection process utilizes two or more high resolution linear color/NIR digital image sensors watching the Foodstuff in the gap between the two belts. The digital image sensors utilize long focal optics to inspect uneven Foodstuff. The software utilized in processing the images of Foodstuff creates a buffer during the image acquisition process and uses object segmentation and color classification with geometrical and morphological contamination filtering to determine if the Foodstuff is a Pass—no Low-Density Foreign Material, or Fail—Low-Density Foreign Material detected.

The entire system is designed to meet IP69 wash-down requirements and is designed for conveyor belts to be removed with no tooling for sanitation. For the purpose of this disclosure, Low-Density Foreign Material can be described as anything that floats and is not detectable by X-ray.

Figure 1:
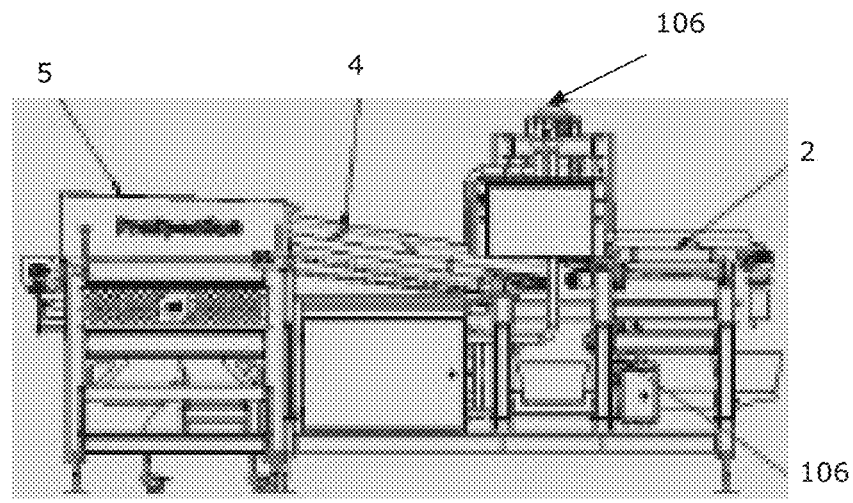
FIG. 1 is a foreign material inspection system according to this disclosure.
Figure 2:
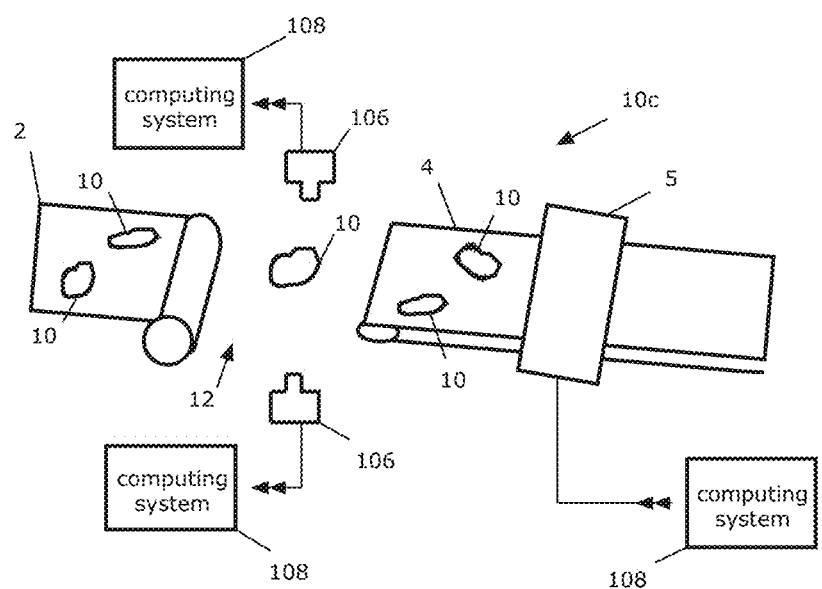
FIG. 2 is a close-up view of the system of FIG. 1.

The inspection system overcomes deficiencies in the prior art by improving upon hand inspection of Foodstuff, which is slow and typically only 30% of the product is inspected. The disclosed 360° Low-Density Foreign Material Inspection System can inspect up to 40,000 lbs. of Foodstuff per hour. It can also inspect all sides of the Foodstuff at the same time, without flipping the Foodstuff. The 360° Low-Density Foreign Material Inspection System automatically tracks the detected Low-Density Foreign Material to the High-Speed Servo Reject System for removal of Contaminated Foodstuff without stopping the production flow. This is a significant improvement over X-ray scanning, which cannot detect Low-Density Foreign Material Referring to FIGS. 1 and 2, shown is a foreign material inspection system 100. System 100 comprises a high-speed servo infeed conveyor 2 and a high-speed exit conveyor 4. A gap 12 between conveyor 2 and conveyor 4 provides an area for viewing by a top camera 106 and a bottom camera 106.

System 100 operates by propelling foodstuff 10 that is placed onto conveyor 2 at a high rate of speed off of conveyor 1 over the gap 12 and onto conveyor 4. While the foodstuff 10 is in the air in the gap 12 between conveyor 2 and conveyor 4, top camera 106 and bottom camera 106 each connected to a processor comprising vision analysis technology captures images of the foodstuff 10. The inspection takes place in the gap 12 in-between conveyor 2 and conveyor 4.

Figure 5:
FIG. 5 is an image taken from the bottom digital image sensor of foodstuff that is processed by the system of FIG. 1.
Figure 6:
FIG. 6 is a composite image taken from both digital image sensors and showing foreign material in the foodstuff.

Top camera 106 and bottom camera 106 can be high-resolution linear color/NIR digital image sensors. Top and bottom cameras 106 watch the foodstuff 10 in the gap 12 between conveyor 2 and conveyor 4. Top and bottom cameras 106 each utilize long focal optics to inspect uneven foodstuff 10. These images are then processed using the vision analysis technology for a determination of foreign material debris 14 (shown in FIG. 5). Foodstuff 10 which contains foreign material debris 14 is then rejected by high-speed servo reject system 5. The software comprising vision analysis technology in the processor creates a buffer during the image acquisition process and uses object segmentation and color classification with geometrical and morphological contamination filtering to determine if the foodstuff 10 is a "Pass" (i.e., no Low-Density Foreign Material) or "Fail" (i.e., Low-Density Foreign Material detected).

Figure 3:
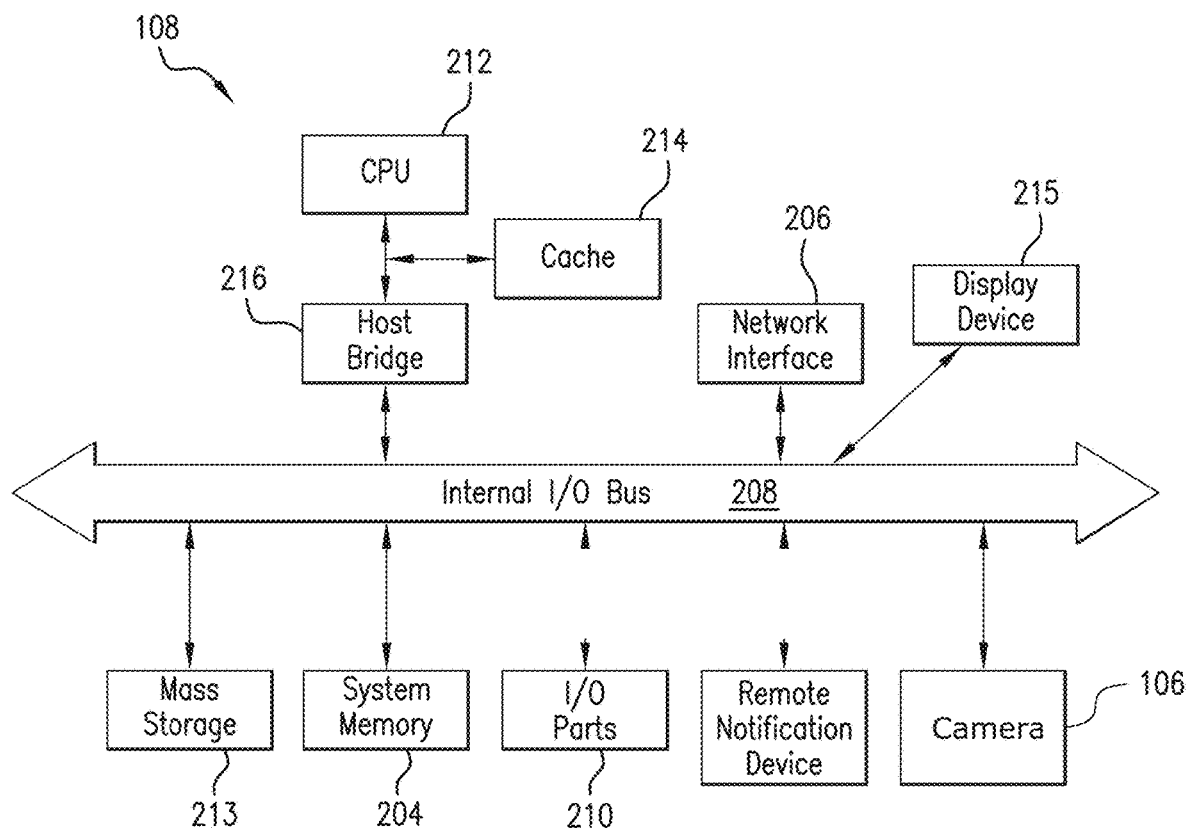
FIG. 3 is a functional block diagram illustrating hardware components of the processor for processing a series of images from an image detector incorporated into the system of FIG. 1.

More specifically, returning to FIG. 2, as shown, the exit of conveyor 2 can be elevated higher than the beginning of conveyor 4 so that the foodstuff 10 that is propelled off conveyor 2 is more likely to land on conveyor 4. The rate of speed of conveyor 2 is easily adjustable to ensure that foodstuff 10 makes it over gap 12 onto conveyor 4. During this period of time, camera 106 and camera 106 capture images of foodstuff 10 in gap 12 for analysis by a computing system 108 (shown in FIG. 3).

Computing system 108 can be a standalone system or incorporated into camera 106 and camera 106. Computing system 108 can receive digital representations of images of foodstuff 10 from camera 106 and camera 106 from a camera 10606. Camera 10606 communicates with one or more processors 212 and a system memory 204. A processor 212 can be included in the same housing as digital image sensor or communicatively coupled as a separate system. A set of instructions can be stored in system memory 204 and executable locally by one or more processors 212. This instruction set can receive a plurality of time-sequenced images 104 of foodstuff 10 from digital image sensor. From these images, computing system 108 can identify foreign debris 14.

Figure 4:
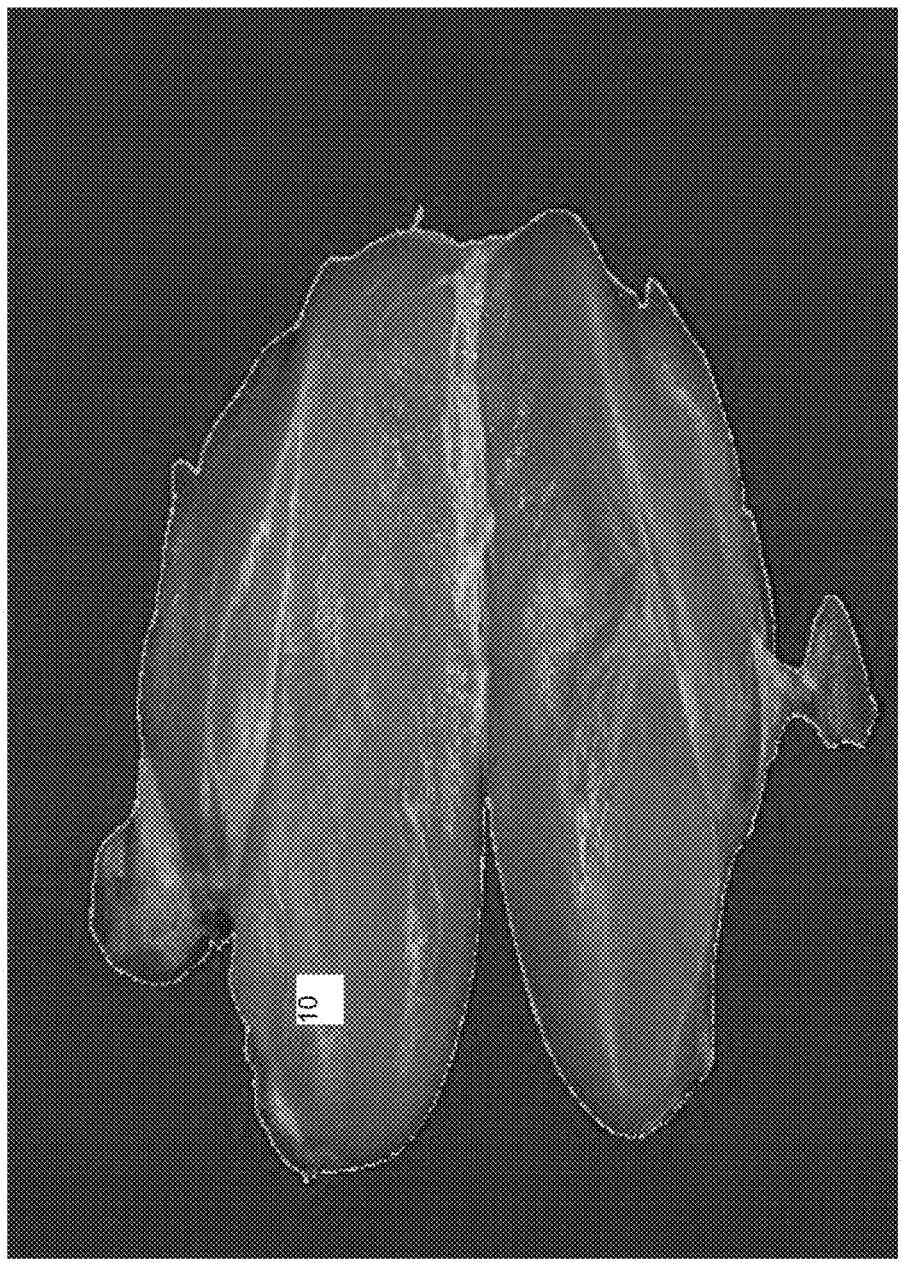
FIG. 4 is an image taken from the top digital image sensor of foodstuff that is processed by the system of FIG. 1.
Figure 7:
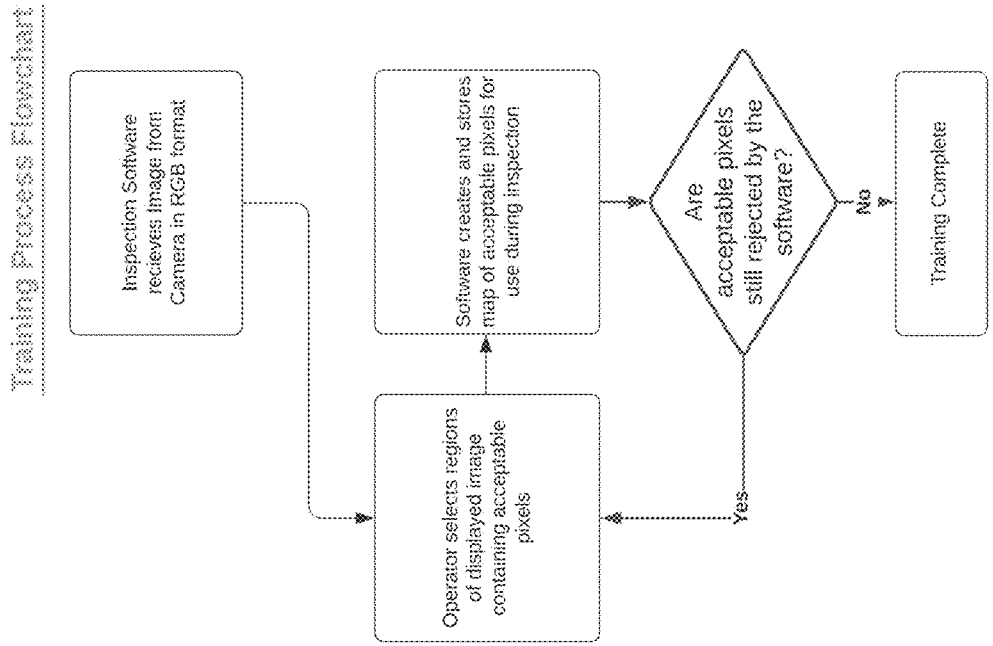
FIG. 7 is flow chart of the training process.

The identification of foreign debris 14 occurs by a comparison of the images with a trained set of images stored in a library. Referring to FIG. 7, which shows the training process, processor 212 receives images from camera 106 in an rgb color format. An operator selects regions of the displayed images containing acceptable pixels, i.e. foodstuff 10. These images and "acceptable pixels" are stored in the library for comparison. System 100 can then be tested by passing foodstuff 10 with known foreign debris 14 therethrough. If "acceptable pixels" are still being flagged by processor 212 as foreign debris then the operator continues the training process by selecting more regions of acceptable pixels. The foregoing process can be better understood by comparison of FIGS. 4-5 which show top and bottom sides of foodstuff 10 without any foreign debris 14 such that all the pixels are considered "acceptable pixels" with FIG. 7 which shows two areas of unacceptable pixels with foreign debris 14. As can be seen in FIG. 7, there are two areas indicative of foreign debris 14 corresponding to pixels from cameras 106 of discoloration and geometric inconsistency that are identified by processor as being inconsistent or "non-matching" to those images stored in the library.

With regards to the inspection process, the software running on processor 212 in computing system 108 utilized in processing the images of foodstuff 10 creates a buffer during the image acquisition process by cameras 106 and uses object segmentation and color classification with geometrical and morphological contamination filtering to identify foreign debris 14 in FIG. 7.

Figure 8:
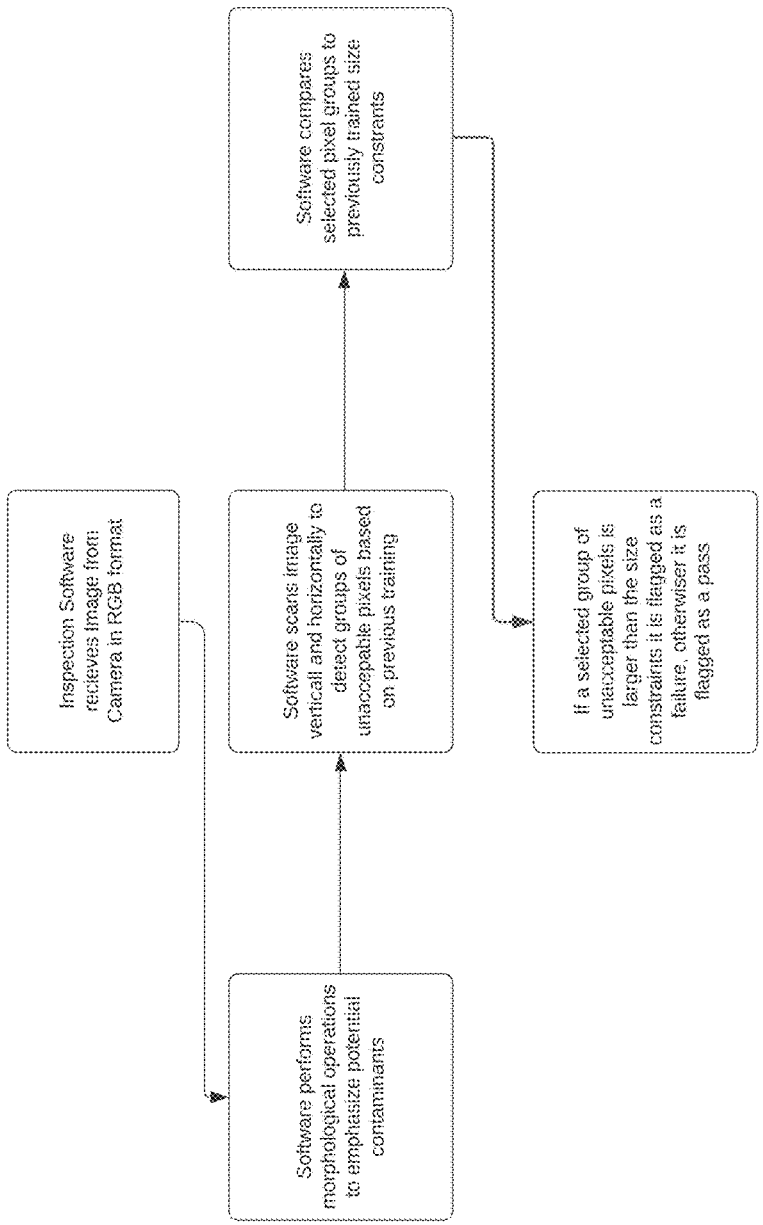
FIG. 8 is a flow chart of the inspection process.

More specifically, referring to FIG. 8, in operation system 100 receives images from cameras 106 in an rgb color format. The software running on processor 212 performs morphological operations to emphasize contaminants. The morphological operations can include, but are not limited to dilation by making objects more visible by setting the output value of a pixel as the maximum value of all pixels in the neighborhood, for example, in a binary image a pixel is set to "1" if any of the neighboring pixels have the value of "1", and erosion by removing islands and small objects so that only substantive objects remain by the reverse of dilation by setting the output value of a pixel as the minimum value of all pixels in the neighborhood.

The software running on processor 212 then scans the digital image vertically and horizontally to detect groups of pixels (i.e., at least two pixels) that are deemed "unacceptable," i.e. that do not match any of the "acceptable pixels" stored in the library. To reduce error of inadvertently rejecting acceptable foodstuff 10, system 100 can compare these groups of pixels to previously trained size constraints. For example, if a group of pixels does not match the minimum number of pixels deemed by training to be foreign debris 14, then it can be disregarded or flagged for manual inspection. If, however, a group of pixels is larger than the size constrains previously determined indicating that the area considered no pass is too large indicating an error, it can be flagged for manual inspection to determine if there's a training error in the software or it could be flagged as a pass and the software could be retrained by using this image as a sample for future recognition, as described above.

System 100 can inspect up to 40,000 lbs. of foodstuff 10 per hour. It can also simultaneously inspect both sides of foodstuff 10 without flipping foodstuff 10. System 100 also automatically tracks foodstuff 10 containing debris 14 to a high-speed servo rejection system 110 for removal of foodstuff 10 that is contaminated with debris 14 without stopping the production flow. This is a significant improvement over X-ray scanning, which cannot detect much of the low density debris commonly found in foodstuffs 10.

When system 100 identifies foodstuff 10 with foreign debris 14, system 100 tracks foodstuff 10 to a high-speed servo rejection system 110 by using the known speed of conveyor 4, the known length of conveyor 4, and the time of image acquisition by top or bottom cameras 106. In order to guarantee the removal of debris 14 the high-speed servo rejection system 110 will open before debris 14 arrives and will close after debris 14 has been removed.

Figure 9:
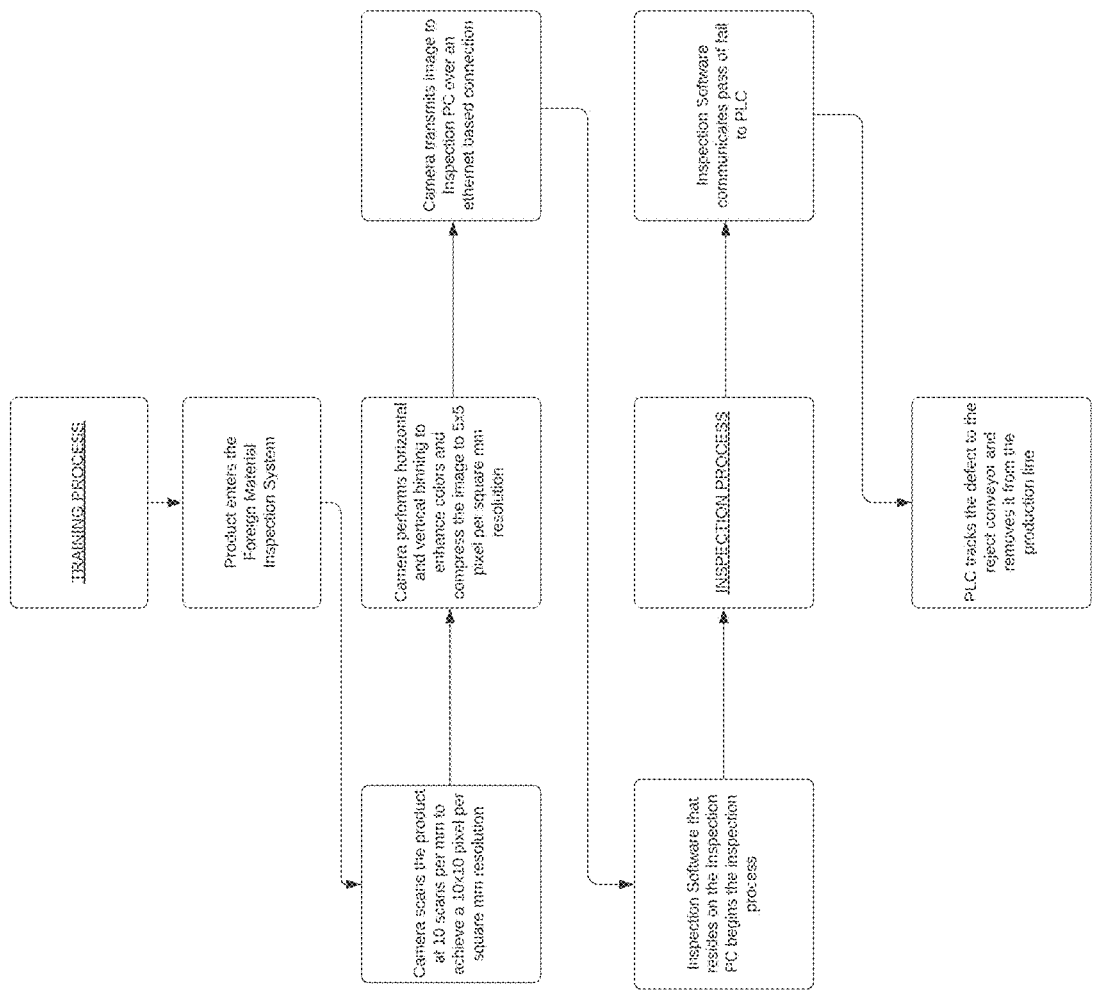
FIG. 9 is a flow chart of the rejection process.

More specifically, referring to FIG. 9, system 100 foodstuff 10 is received with cameras 106 scan foodstuff 10 at a rate of ten scans per millimeter to obtain a 10×10 pixels per square millimeter resolution. The images are scanned horizontally and vertically to enhance colors and compress the image to a 5×5 pixel per square millimeter resolution for the inspection process described above. The output of the process, i.e. a "pass" or fail" is communicated to a programmable logic controller inside rejection system 110 which tracks the "fail" foodstuff 10 to the reject conveyor for removal from the product line.

Processor 212 is housed in an exemplary computing platform for executing the processing function necessary to derive, calculate, and perform the above functions that are described as being carried out on processor 212. In one implementation, processor 212 comprises a system memory 204, network interface 206 and one or more software applications and drivers enabling or implementing the methods and functions described herein. Hardware system includes a standard I/O bus 208 with I/O Ports 210 and mass storage 213 (which can also be a non-volatile Flash Memory) coupled thereto or external or cloud-based storage, such as the Google or Amazon cloud services. Bridge 216 couples processors 212 to I/O bus 208. The hardware system may further include video memory and display device 215 coupled to the video memory. These elements are intended to represent a broad category of computer hardware systems, including but not limited to general-purpose computer systems based on the Pentium processor manufactured by Intel Corporation of Santa Clara, Calif., as well as any other suitable processor.

Elements of the computer hardware system perform their conventional functions known in the art. In particular, network interface 206 is used to provide communication between processors 212 and Ethernet networks (or any other network or external device). Mass storage 213 can be provided and used to provide permanent storage for the data and programming instructions to perform the above-described functions implementing the test to be carried, whereas system memory 204 (e.g., DRAM) is used to provide temporary storage for the data and programming instructions when executed by processors 212. I/O ports 210 are one or more serial and/or parallel communication ports used to provide communication between additional peripheral devices, such as top and bottom cameras 106.

For the purpose of this disclosure, top and bottom cameras 106 include any analog or digital camera or any analog or digital image sensor capable of capturing colored rbg images visible to the human eye. Such sensors include CCD and CMOS technology. For the purpose of this disclosure, when it is stated that top and bottom cameras 106 take simultaneous images of the respective top side and the bottom side of the foodstuff, simultaneous is being in the time range that the foodstuff is airborne between the first conveyor 2 and the second conveyor 4.

Computing system 108 may include a variety of system architectures, and various components of processors 212 may be rearranged. For example, cache 214 may be on-chip with processors 212. Alternatively, cache 314 and processors 212 may be packed together as a "processor module," with processors 212 being referred to as the "processor core." Furthermore, certain implementations of the claimed embodiments may not require nor include all the above components. Also, additional components may be included, such as additional processors, storage devices, or memories.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

We claim:
1. A foodstuff inspection system, comprising:
a first conveyor for conveying foodstuff;
a second conveyor separated from the first conveyor by a gap of free space;
a top rgb camera positioned above the gap and above the first conveyor and the second conveyor;
a bottom rgb camera positioned below the gap and below the first conveyor and the second conveyor; and
wherein the top rgb camera and the bottom rgb camera capture rgb images of the foodstuff in the gap between the first conveyor and the second conveyor for analysis, and wherein the top rgb camera and the bottom rgb camera capture colored rgb images for analysis;
a processor connected to the top rgb camera and the bottom rgb camera for processing rgb images taken of the foodstuff for detection of foreign debris in the foodstuff;
a library communicatively coupled to the processor containing each of the RGB components of data representative of acceptable rgb pixels corresponding to rgb images of foodstuff wherein the processor compares rgb images of the foodstuffs on a pixel by pixel basis with the data representative of each of the RGB components of acceptable rgb pixels stored in the library to detect foreign debris, wherein the processor conducts a morphological operation on the image of the foodstuff to emphasize foreign debris before the processor compares the image of the foodstuff, and wherein the morphological operation comprises image dilation to make foreign debris more visible by setting an output value of a rgb pixel as either a maximum or minimum value of all neighboring rgb pixels.

2. The food inspection system of claim 1, wherein the processor scans the rgb image of the foodstuff both vertically and horizontally to detect groups of adjacent rgb pixels corresponding to foreign debris.

3. The food inspection system of claim 2, wherein the group of adjacent rgb pixels below a threshold number of rgb pixels is ignored.

4. The food inspection system of claim 1, wherein the top rgb camera and the bottom rgb camera take simultaneous rgb images of the respective top side and the bottom side of the foodstuff.

5. The food inspection system of claim 1, and further comprising a rejection system communicatively coupled to a processor wherein when a group of rgb pixels in the rgb image of the foodstuff is determined to be consistent with foreign debris, the foodstuff is tracked by the rejection system for removal.

6. The food inspection system of claim 5, wherein the rejection system uses the speed of the second conveyor, the length of the second conveyor, and the time of acquisition of the image of the foodstuff to track the foodstuff for removal.

7. The food inspection system of claim 1, wherein top rgb camera and the bottom rgb camera take rgb images of the foodstuff while the foodstuff is in mid air between the first conveyor and the second conveyor.

8. The food inspection system of claim 7, wherein the top side of the first conveyor is elevated higher from the ground than the top side of the bottom conveyor to aid the transition of the foodstuff from the first conveyor to the second conveyor.

9. A method of food inspection comprising:
transporting foodstuff on a first conveyor and a speed sufficient to transport the foodstuff over a gap onto a second conveyor;
photographing rgb images of the foodstuff from the top with a top rgb camera positioned above the gap and above the first conveyor and the second conveyor, and from the bottom with a bottom rgb camera positioned below the gap and below the first conveyor and the second conveyor while the foodstuff is in the gap between the first conveyor and the second conveyor; and
determining from the rgb images of the foodstuff the presence of foreign debris in the foodstuff;
photographing rgb images of the foodstuff simultaneously with the top rgb camera and the bottom rgb camera;
conducting a morphological operation on the image of the foodstuff to emphasize foreign debris by setting an output value of a rgb pixel as either a maximum or minimum value of all neighboring rgb pixels;
comparing rgb images of the foodstuffs on a pixel by pixel basis with data representative of each of the RGB components of acceptable rgb pixels; and
scanning each of the rgb images of the foodstuff horizontally and vertically to identify groupings of pixels indicative of foreign debris in the foodstuff.

10. The method of claim 9, and further comprising comparing each rgb pixel in each of the rgb images of the foodstuff with data representative of acceptable rgb pixels stored in a library of acceptable rgb pixels.

11. The method of claim 10, and further comprising processing the rgb images of the foodstuff to emphasize foreign debris before the comparing the rgb image of the foodstuff with data in the library of acceptable rgb pixels; ignoring the group of adjacent rgb pixels not matching the data in the library of acceptable rgb pixels below a threshold number of rgb pixels; and rejecting the foodstuff corresponding to the rgb images of the foodstuff having the group of adjacent rgb pixels not matching the data in the library of acceptable rgb pixels.

12. The food inspection system of claim 1, wherein the bottom rgb camera is oriented upward with a field of view oriented upward toward the gap to directly capture bottom images of the foodstuff while in the gap.

13. The food inspection system of claim 1, wherein the bottom rgb camera is oriented completely below the gap and directly imaging the bottom of the foodstuffs.

14. The food inspection system of claim 1, wherein the top conveyor comprises a plane on which the foodstuff sits and the bottom conveyor comprises a plane on which the foodstuff sits; wherein the plane of the top conveyor is above the plane of the bottom conveyor; and wherein the rgb camera is positioned below the plane of the bottom conveyor and oriented vertically upward with a field of view capturing the horizontal width of the gap to directly image the bottom of the foodstuffs while in the gap.

15. The food inspection system of claim 1, wherein the bottom rgb camera is positioned immediately below the gap and oriented upward to directly image the bottom of the foodstuffs while in the gap.

* * * * *

UNITED STATES PATENT AND TRADEMARK OFFICE
CERTIFICATE OF CORRECTION

| | | |
|---|---|---|
| PATENT NO. | : 12,106,468 B2 | |
| APPLICATION NO. | : 17/061217 | |
| DATED | : October 1, 2024 | |
| INVENTOR(S) | : Jeff Youngs, Kyle N. Knudsen and Filippo Sani | |

It is certified that error appears in the above-identified patent and that said Letters Patent is hereby corrected as shown below:

On the Title Page

Item [72], the word "Flippo" should be corrected to "Filippo"

Signed and Sealed this
Twelfth Day of November, 2024

*Katherine Kelly Vidal*

Katherine Kelly Vidal
*Director of the United States Patent and Trademark Office*